US010922735B2

(12) United States Patent
Porter

(10) Patent No.: US 10,922,735 B2
(45) Date of Patent: Feb. 16, 2021

(54) SYSTEM AND METHOD OF PROVIDING CUSTOMIZED HAIR CARE INFORMATION

(71) Applicant: Crystal Elaine Porter, Bolingbrook, IL (US)

(72) Inventor: Crystal Elaine Porter, Bolingbrook, IL (US)

( * ) Notice: Subject to any disclaimer, the term of this patent is extended or adjusted under 35 U.S.C. 154(b) by 382 days.

(21) Appl. No.: 14/276,991

(22) Filed: May 13, 2014

(65) Prior Publication Data

US 2014/0337333 A1 Nov. 13, 2014

Related U.S. Application Data

(60) Provisional application No. 61/822,788, filed on May 13, 2013.

(51) Int. Cl.
| | |
|---|---|
| *G06Q 30/00* | (2012.01) |
| *G06Q 30/06* | (2012.01) |
| *A61B 5/00* | (2006.01) |

(52) U.S. Cl.
CPC ......... *G06Q 30/0631* (2013.01); *A61B 5/448* (2013.01)

(58) Field of Classification Search
CPC .............. G06F 17/30; G06F 17/30867; G06F 19/3456; G06Q 30/0631; G06Q 50/22; A61B 5/448
USPC .......................................... 707/733, 754, 758
See application file for complete search history.

(56) References Cited

U.S. PATENT DOCUMENTS

| | | | |
|---|---|---|---|
| 7,437,344 B2 | 10/2008 | Peyrelevade | |
| 7,806,121 B2* | 10/2010 | Bodduluri | G06F 19/3437 606/133 |
| 8,988,686 B2* | 3/2015 | Hillebrand | A45D 44/005 356/421 |
| 9,222,836 B2* | 12/2015 | Conti | G01J 3/0202 |
| 2003/0064350 A1 | 4/2003 | Rubinstenn et al. | |
| 2003/0065636 A1 | 4/2003 | Peyrelevade | |
| 2004/0179736 A1* | 9/2004 | Yin | G06K 9/00342 382/191 |

(Continued)

FOREIGN PATENT DOCUMENTS

| | | |
|---|---|---|
| JP | 2000128739 A | 5/2000 |
| JP | 2002136503 A | 5/2002 |
| WO | 2004042510 A2 | 5/2004 |

*Primary Examiner* — Vincent F Boccio
(74) *Attorney, Agent, or Firm* — Jason P. Webb; Pearson Butler

(57) ABSTRACT

A system and method of providing customized hair care information including the step of gathering data on an individual's hair. The system and method includes the step of creating, within a computerized system, an account. The system and method includes storing the gathered data in association with the account in a computerized data storage device. The system and method include the step of analyzing the stored data using a processor in association with a computerized knowledge base thereby generating account analytics. The step of analyzing stored data from a plurality of diverse accounts includes the step of grouping the analyzed stored data by at least one category selected from the group of categories consisting of: race/ethnicity, hair color, hair composition, hair style, hair length, hair thickness, and hair curliness. The system and method includes automatically generating a customized hair report based on the account analytics.

20 Claims, 3 Drawing Sheets

(56) References Cited

U.S. PATENT DOCUMENTS

| | | | | |
|---|---|---|---|---|
| 2005/0240085 A1* | 10/2005 | Knoell | .................. | A61B 5/411 |
| | | | | 600/300 |
| 2006/0265244 A1* | 11/2006 | Baumann | ............... | G06Q 30/02 |
| | | | | 424/401 |
| 2008/0294018 A1* | 11/2008 | Kurtz | ..................... | A61B 5/103 |
| | | | | 600/301 |
| 2009/0076639 A1* | 3/2009 | Pak | ........................ | G06Q 10/08 |
| | | | | 700/106 |
| 2012/0041282 A1* | 2/2012 | Nichol | ................ | A61B 5/0002 |
| | | | | 600/306 |
| 2013/0057866 A1* | 3/2013 | Hillebrand | .......... | A45D 44/005 |
| | | | | 356/421 |
| 2013/0218474 A1* | 8/2013 | Longo | .............. | G01N 33/56972 |
| | | | | 702/19 |
| 2014/0344102 A1* | 11/2014 | Cooper | ............. | G06Q 30/0631 |
| | | | | 705/26.7 |

* cited by examiner

SYSTEM AND METHOD OF PROVIDING CUSTOMIZED HAIR CARE INFORMATION

CROSS-REFERENCE TO RELATED APPLICATIONS

This invention claims priority, under 35 U.S.C. § 120, to the U.S. Provisional Patent Application No. 61/822,788 to Crystal E. Porter filed on May 13, 2013, which is incorporated by reference herein.

BACKGROUND OF THE INVENTION

Field of the Invention

The present invention relates to hair care, specifically to a system and method of providing customized hair care information.

Description of the Related Art

Currently, known consultants for hair care advice and characterization for the public are cosmetologist, bloggers and dermatologists. Cosmetologists use their expertise from styling experience and knowledge based on the aesthetics of hair from visual and tactile assessments. They use techniques such as pulling on the hair to qualify porosity and elasticity and they look at the hair to determine the quality. However, they do not have in-depth knowledge about the scientific implications of their practices and do not quantify physical characteristics of hair as a part of their services.

The popularity of support groups that are available on the internet has given rise to expert bloggers who disseminate information about issues that are relevant to the masses. Professional bloggers have become renowned and have a faithful following because they appeal to the public by discussing topics that pertain to hair health, common problems and styling recommendations. They obtain their information from popular cosmetologists and written articles that pertain to hair science. Just like cosmetologist and trichologists, they usually have limited or even erroneous information about the scientific aspect of hair and none of them provide services that are individualized.

Dermatologists are physicians who specialize in the care of skin and hair. They use evidence-based medical research to treat and advise patients about best practices and care for specific diagnosed ailments. They usually obtain knowledge about hair care from personal interactions with their patients, published literature and some perform clinical studies looking at the effects of drug interactions and use techniques such as scalp biopsies, amino acid analysis and microscopy. Because of the scientific nature of research, it is imperative that reported results come from diverse populations in order for studies to be valid. However, dermatologists often make recommendations based on outdated findings or limited information because they do not routinely ask detailed questions about hair grooming practices or understand the effects of products to give comprehensive advice about hair care to their patients.

Standard hair analyses are performed by consulting firms and universities that provide services for companies within the cosmetics industry for mostly claims and sometimes research purposes. They perform a variety of physical and chemical assessments to study hair characteristics and determine the effects of a variety of environmental variables. Currently, these analyses are not marketed for the public.

Some improvements have been made in the field. Examples of references related to the present invention are described below in their own words, and the supporting teachings of each reference are incorporated by reference herein:

U.S. Pat. No. 7,437,344, issued to Peyrelevade, discloses using an artificial intelligence engine to provide beauty advice. Beauty advice may include a recommendation for a product. The recommended product may be complementary to a second product. The second product may be a user-selected product. A notification of the recommended product may be provided to the user.

U.S. Patent Application Publication No.: 2003/0065636, by Peyrelevade, discloses using an artificial intelligence engine to provide beauty advice. Beauty advice may include a recommendation for a product. The recommended product may be complementary to a second product. The second product may be a user-selected product. A notification of the recommended product may be provided to the user.

U.S. Patent Application Publication No.: 2003/0064350, by Rubinstenn, discloses systems and methods consistent with the invention may provide beauty advice. Personal information about a subject may be obtained. The personal information may include at least demographic information about the subject. The demographic information may include a geographic location of the subject. Based on the demographic information, local information may be determined. Then, based on the personal information and the local information, at least one recommendation for use of at least one beauty product may be generated and presented.

The inventions heretofore known suffer from a number of disadvantages which include being limited in application, being un-scientific, failing to improve across a plurality of populations, being ineffective, being randomly-effective, being limited in organization, being limited in use, being limited in capabilities, being limited in categorization, being un-collaborative and/or the like.

What is needed is a system or method of providing customized hair care information that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available systems and methods of providing customized hair car information. Accordingly, the present invention has been developed to provide a customized hair care system and method.

According to one embodiment of the invention, there is a method of providing customized hair care information including the step of gathering data on an individual's hair. The step of gathering data may include the step of gathering a hair sample; conducting an interview with an individual; or completing a questionnaire based upon an individual's hair. The method may include the step of creating, within a computerized system, an account.

The method may include storing the gathered data in association with the account in a computerized data storage device. The step of storing the gathered data may include the step of automatically storing the gathered data with an account, over a computerized network. The method may include the step of analyzing the stored data using a processor in association with a computerized knowledge base thereby generating account analytics. The step of analyzing stored data from a plurality of diverse accounts may include the step of grouping the analyzed stored data by at least one category selected from the group of categories consisting of: race/ethnicity, hair color, hair composition, hair style, hair length, hair thickness, and hair curliness.

The method may also include the step of automatically generating a customized hair report based on the account analytics. The method of providing customized hair care information may include the step of analyzing stored data from a plurality of diverse accounts thereby generating group account analytics. The method may include the step of automatically publishing information associated with account analytics over a computerized network.

According to one embodiment of the invention, there is a system of providing customized hair care information that may include an account module that may store hair data in association with a plurality of accounts. The system may include a knowledge base module that may include executable information regarding hair. The system may include an analytics module that may be in communication with each of the account module and the knowledge base module and may analyze collections of hair data according to the executable information regarding hair. The analytics module may analyze stored data from a plurality of diverse accounts thereby generating group account analytics.

The system may include a report module that may be in communication with the analytics module that may automatically generates a report including analysis information from the analytics module. The report module may be in communication with the account module. The report module may automatically send the report to an electronic address listed within the account module that may be associated with the hair data analyzed in the report. The report module may group the analyzed stored data by at least one category selected from the group of categories consisting of: race/ethnicity, hair color, hair composition, hair style, hair length, hair thickness, and hair curliness.

The system may include a data collection device that may be in communication with the account module and may automatically collects data on hair samples and delivers such data to the account module. The system may include a publication module that may be in communication with the report module that may publish report information to a plurality of electronic addresses. The system may include a questionnaire module that may include an electronic questionnaire functionally coupled to the account module.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which.

DETAILED DESCRIPTION OF THE INVENTION

Figure 1:
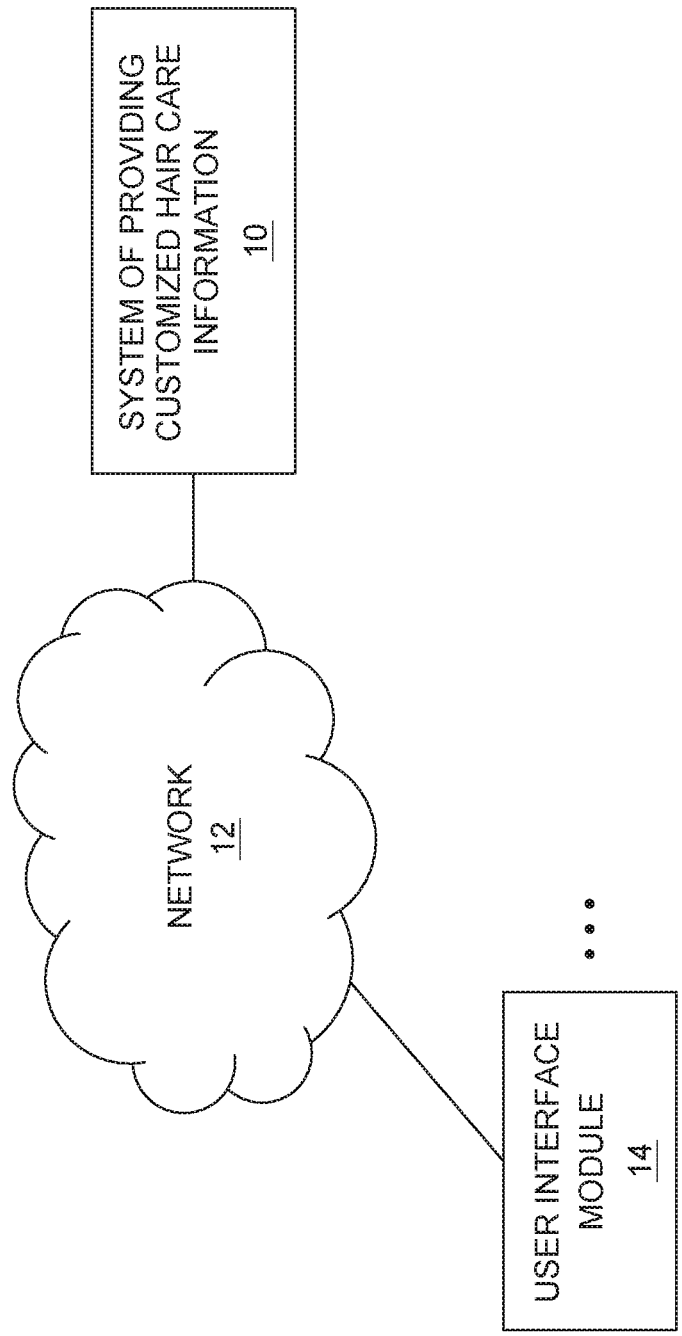
FIG. 1 is a network diagram of a system and method of providing customized hair care information, according to one embodiment of the invention.

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Many of the functional units described in this specification have been labeled as modules in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like. Modules may also be implemented in software for execution by various types of processors. An identified module of programmable or executable code may, for instance, comprise one or more physical or logical blocks of computer instructions which may, for instance, be organized as an object, procedure, or function.

Nevertheless, the executables of an identified module need not be physically located together, but may comprise disparate instructions stored in different locations which, when joined logically together, comprise the module and achieve the stated purpose for the module. Indeed, a module and/or a program of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

The various system components and/or modules discussed herein may include one or more of the following: a host server, motherboard, network, chipset or other computing system including a processor for processing digital data; a memory device coupled to a processor for storing digital data; an input digitizer coupled to a processor for inputting digital data; an application program stored in a memory device and accessible by a processor for directing processing of digital data by the processor; a display device coupled to a processor and/or a memory device for displaying information derived from digital data processed by the processor; and a plurality of databases including memory device(s) and/or hardware/software driven logical data storage structure(s).

Various databases/memory devices described herein may include records associated with one or more functions, purposes, intended beneficiaries, benefits and the like of one or more modules as described herein or as one of ordinary skill in the art would recognize as appropriate and/or like data useful in the operation of the present invention.

As those skilled in the art will appreciate, any computers discussed herein may include an operating system, such as but not limited to: Andriod, iOS, BSD, IBM z/OS, Windows Phone, Windows CE, Palm OS, Windows Vista, NT, 95/98/ 2000, OS X, OS2; QNX, UNIX; GNU/Linux; Solaris; MacOS; and etc., as well as various conventional support software and drivers typically associated with computers. The computers may be in a home, industrial or business environment with access to a network. In an exemplary embodiment, access is through the Internet through a commercially-available web-browser software package, including but not limited to Internet Explorer, Google Chrome, Firefox, Opera, and Safari.

The present invention may be described herein in terms of functional block components, functions, options, screen shots, user interactions, optional selections, various processing steps, features, user interfaces, and the like. Each of such described herein may be one or more modules in exemplary embodiments of the invention even if not expressly named herein as being a module. It should be appreciated that such functional blocks and etc. may be realized by any number of hardware and/or software components configured to perform the specified functions. For example, the present invention may employ various integrated circuit components, e.g., memory elements, processing elements, logic elements, scripts, look-up tables, and the like, which may carry out a variety of functions under the control of one or more microprocessors or other control devices. Similarly, the software elements of the present invention may be implemented with any programming or scripting language such as but not limited to Eiffel, Haskell, C, C++, Java, Python, COBOL, Ruby, assembler, Groovy, PERL, Ada, Visual Basic, SQL Stored Procedures, AJAX, Bean Shell, and extensible markup language (XML), with the various algorithms being implemented with any combination of data structures, objects, processes, routines or other programming elements. Further, it should be noted that the present invention may employ any number of conventional techniques for data transmission, signaling, data processing, network control, and the like. Still further, the invention may detect or prevent security issues with a client-side scripting language, such as JavaScript, VBScript or the like.

Additionally, many of the functional units and/or modules herein are described as being "in communication" with other functional units, third party devices/systems and/or modules. Being "in communication" refers to any manner and/or way in which functional units and/or modules, such as, but not limited to, computers, networks, mobile devices, program blocks, chips, scripts, drivers, instruction sets, databases and other types of hardware and/or software, may be in communication with each other. Some non-limiting examples include communicating, sending, and/or receiving data and metadata via: a wired network, a wireless network, shared access databases, circuitry, phone lines, internet backbones, transponders, network cards, busses, satellite signals, electric signals, electrical and magnetic fields and/or pulses, and/or so forth.

As used herein, the term "network" includes any electronic communications means which incorporates both hardware and software components of such. Communication among the parties in accordance with the present invention may be accomplished through any suitable communication channels, such as, for example, a telephone network, an extranet, an intranet, Internet, point of interaction device (point of sale device, personal digital assistant, cellular phone, kiosk, etc.), online communications, off-line communications, wireless communications, transponder communications, local area network (LAN), wide area network (WAN), networked or linked devices and/or the like. Moreover, although the invention may be implemented with TCP/IP communications protocols, the invention may also be implemented using other protocols, including but not limited to IPX, Appletalk, IP-6, NetBIOS, OSI or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA 2 COMPLETE, various authors, (Sybex 1999); DEBORAH RAY AND ERIC RAY, MASTERING HTML 4.0 (1997); and LOSHIN, TCP/IP CLEARLY EXPLAINED (1997), the contents of which are hereby incorporated by reference.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

FIG. 1 is a network diagram of a system and method of providing customized hair care information, according to one embodiment of the invention. There is shown a system for providing customized hair care information 10 in communication with a plurality of user interface modules 14 over a computerized network 12. The illustrated system advantageously provides customized hair care information to individuals, wherein such information may be utilized in concert with other hair care efforts, such as but not limited to those provided by hair care professionals.

The illustrated system 10 is configured to provide customized hair care information to users over a computerized network 12. Users (e.g. individuals themselves, hair care professionals) gather hair data and input the data into the system 10 by a user interface module 14, such as but not limited to a personal computer, a smart-phone application, a dedicated terminal, a user interface functionally coupled to a data sampling device, a kiosk, a tablet computing device and the like and combinations thereof that are functionally coupled to the system and/or integral to the same. The system 10 stores and analyzes the hair data received therein against a knowledge base functionally coupled to and/or integral to the system, and then automatically generates and publishes customized hair care information in the form of a report (e.g. in the form of a pdf file emailed to an email address associated with a user account linked to the hair data). The report is detailed specifically to the user or a group of users with similar hair characteristics.

According to one embodiment of the invention, the system and method involves collecting information about different aspects of hair care practices in order to: 1) provide hair advice to the general public for those who request it based on scientific information obtained, and 2) generate detailed analysis of data related to consumers and hair properties for professionals who serve clientele in regards to hair which include but not limited to physicians such as dermatologists and cosmetologists/trichologists.

The system offers advice, services or ideas based on data, private consultation and/or hair samples provided by the customer. The system guides the customer to receive information and/or advice that is specific to individual needs. The system provides a customized report that may be manually customized and/or automatically generated by a program that receives the information in written, verbal and/or electronic form. The system may automatically convert input to various forms (e.g. voice-to-text conversion, text entry to structured database, structured database to voice). The system automatically generates visual tools (that may be interactive) and feedback in the form of graphics, animation, movies, photos, and/or voice to communicate information in the report, thus the report may include a multimedia experience that may be interactive.

The system may do one or more of: 1) provide a service to the public to learn how to modify their hair routines to improve the condition of their hair based on individuals needs and 2) provide clinical and consumer information to professionals to give more comprehensive data that is relevant for their respective businesses. The system and method may provide detailed information (e.g. demographic, hair care conditions/practices, location, hair care history, health history) about those associated with hair data to provide a scientific approach to hair care.

Individuals and/or professionals may contact the system via internet or in-person and pay for tailored hair-care advice based on consumer and/or scientific information from analysis. The system may provide for completion a detailed questionnaire about the demographic background, grooming routine, primary geographic location, product uses, habits and practices of those requesting services and/or submitting hair samples for testing. Questionnaires may be presented by the system such that they may be answered in electronic, verbal and/or written form and the information will be put into a module that stores and/or processes the same, such as but not limited to survey/questionnaire tools such as but not limited to those provided under the brand Survey Monkey at www.surveymonkey.com. The data is studied or processed through a computer program (yet to be developed) and a tailored report will be generated and submitted to the customer.

Customers have the option of having their hair or their client's hair analyzed for more in-depth knowledge about their hair quality. This may involve the use of various instruments and techniques such as the following but not limited to: a tensile tester such as a Diastron Model MTT175 or equivalent, a micrometer such as a Diastron Model FDAS765, a stereo microscope such as a Hirox KH 1300 video microscope or equivalent, a relative hair density test using an SG-Ultra-Max digital hydrometer/density meter or equivalent, and porosity using a Micromeritics ASAP 2020 gas sorption instrument or equivalent or dye-penetration experiments. Information from the generated results may be supplemented and incorporated into the tailored report to provide comprehensive details about unique hair qualities. Such instruments may be functionally coupled to the system such that data obtained therefrom may be automatically provided to the system and/or automatically associated with a particular user account.

After hair samples are obtained, fibers may be cleaned using a 10% ammonium lauryl sulfate solution or the like. The hair may be tested using the techniques listed above and the following information about the hair may be generated/obtained by the system: tensile strength, plateau load, plateau stress, post-yield modulus, load at 15% strain, stress at 15% strain, load at 25% strain, stress at 25% strain, work at 15% strain, work at 25% strain, break load, break stress, break extension, average diameter, average cross-sectional area, minimum diameter, minimum cross-sectional area, maximum diameter, maximum cross-sectional area, ellipticity, and twisting frequency, hair micrographs (images), hair density, porosity and the like and combinations thereof. Data may be generated in the form of tables of information, graphics, animation, movies, and/or photos and such may be provided with the report.

Such data may be stored within the system and/or incorporated into a knowledge base within the system. Such data may be anonymized during an archival process so that demographic information is preserved but individuating/identifying information is removed or encrypted. As a result of the data generated, data analytics may be performed using Intel Big Data Mining or equivalent as a basis for scientific research to understand even more specifics about how the different variables such as product brands, new processes and new treatments influence hair properties.

Figure 2:
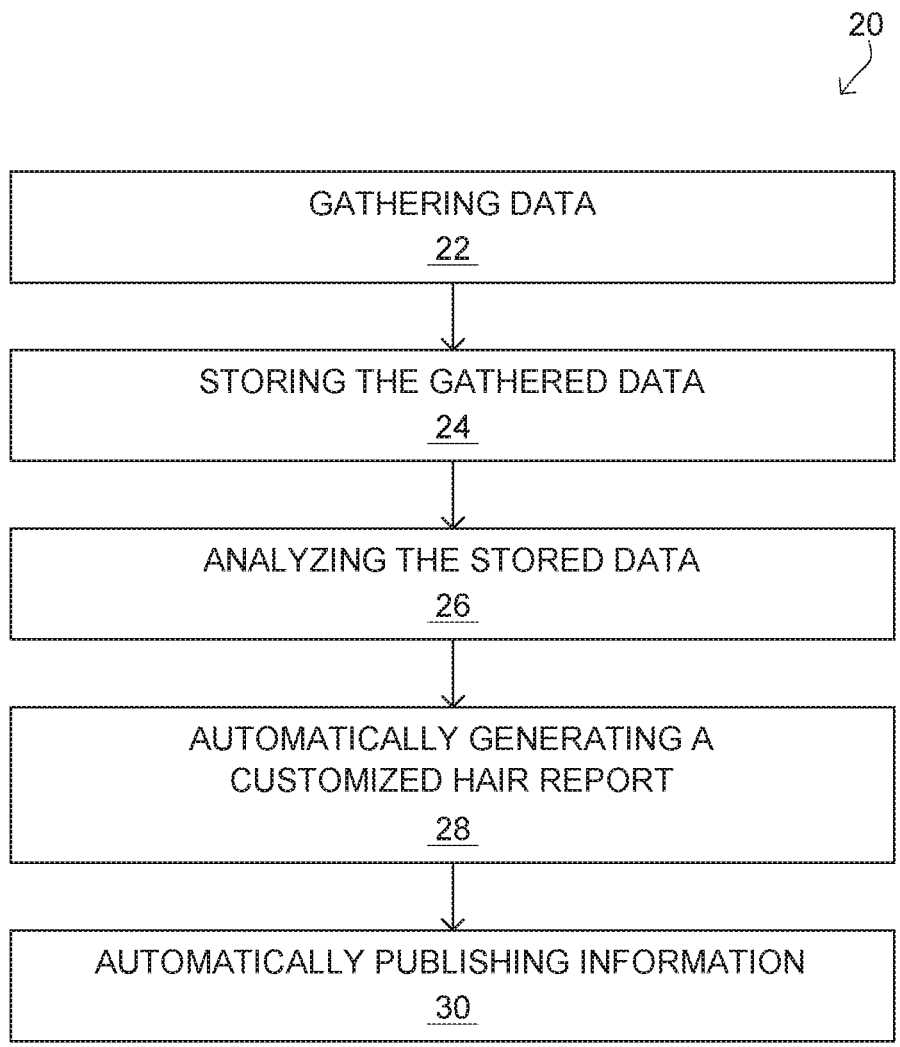
FIG. 2 is a flow chart of a method of providing customized hair care information, according to one embodiment of the invention.

FIG. 2 is a flow chart of a method of providing customized hair care information, according to one embodiment of the invention. There is shown a method of providing customized hair care information 20 including the steps of gathering, storing and analyzing data; automatically generating a customized hair report; and automatically publishing information. Advantageously, such a method allows for consistent and scientific treatment of hair and hair care that may be easily integrated into existing hair care practices in association with existing hair care professionals. The method may be easily operated in a centralized manner without requiring additional space in retail establishments or the establishment of deployment offices across a large geographic region.

The illustrated method of providing customized hair care information 20 includes the step of gathering data on an individual's hair 22. The step of gathering data 22 includes the step of gathering a hair sample; conducting an interview with an individual; and completing a questionnaire based upon an individual's hair. The method 20 includes the step of creating, within a computerized system, an account intended to be associated with a particular hair sample and/or set of the same. The step may include providing an electronic questionnaire to an individual over an electronic device that may be coupled to a system for providing customized hair care information over a network. The step may include providing a mailer and/or instructions for obtaining a hair sample from an individual and/or for submission of the sample to the system.

The method 20 includes storing the gathered data in association with the account in a computerized data storage device 24 such as but not limited to storing the same within a structured database and including an account identifier within the same and associated with such data so that the data may be retrieved when indexed according to the account information. Such information may be stored by date and/or batch number so that the same user or user group may include multiple instances of hair data that may be correlated. The step of storing the gathered data 24 includes the step of automatically storing the gathered data with an account, over a computerized network. Such may be accomplished by use of devices that automatically acquire data using computing device(s) and that are in communication with the data storage of the system so that the same may be automatically populated into the data storage. As a non-limiting example, each mailer may include a machine readable identifier that may, through the system, automatically generate a new batch and/or account when read. Subsequent information regarding the hair sample may be associated with the machine readable identifier and thusly associate with the batch and/or account. A batch may be initially associated with an account so that all data associated with a batch may be automatically associated with the account as well.

The method 20 includes the step of analyzing the stored data 26 using a processor in association with a computerized knowledge base thereby generating account analytics. The step of analyzing stored data 26 from a plurality of diverse accounts includes the step of grouping the analyzed stored data by at least one category selected from the group of categories consisting of: race/ethnicity, hair color, hair composition, hair style, hair length, hair thickness, and hair curliness. Such may also include automatically comparing, contrasting, correlating, indexing, searching and/or otherwise accessing a knowledge base module to automatically obtain additional information that may then be automatically associated with a batch and/or account. As a non-limiting example, the system may search the knowledge base for similar prior hair samples that observed positive changes after specific treatments and then may include such treatments in a list of possible recommendations. The step of analyzing may include having an expert review results of the analysis for adjustment, further customization, and the like which may be manually adjusted and stored along with the rest of the information in the account.

The method 20 includes the step of automatically generating a customized hair report based on the account analytics 28. Analytic results, including but not limited to manual entries/modifications by an expert, may be processed into a report format that may be automatically generated according to a template. The report may include hair data information and/or a summary thereof. The report may include specific recommendations. The report may mention areas of concern. The report may highlight specific aspects of the hair data that are particularly favorable. The report may include suggestions. The report may suggest specific products, categories of products, treatments, interventions, warnings, suggestions for medical treatment/review or the like.

The method of providing customized hair care information 20 includes the step of analyzing stored data from a plurality of diverse accounts thereby generating group account analytics. Such may include storing account data and/or portions thereof in an aggregated/archived manner that allows for data mining and/or population of a knowledge base module. Thus, the system may continually improve by feeding the knowledge base with additional information as the system/method continues to operate.

The method 20 includes the step of automatically publishing information associated with account analytics over a computerized network 30. Such may include sending a report to a person associated with an account, a group of people, a set of professionals, and the like and combinations thereof. Such may be accomplished by automatically posting to a blog, emailing a report, feeding a data set over a network to a related system and the like and combinations thereof.

Figure 3:
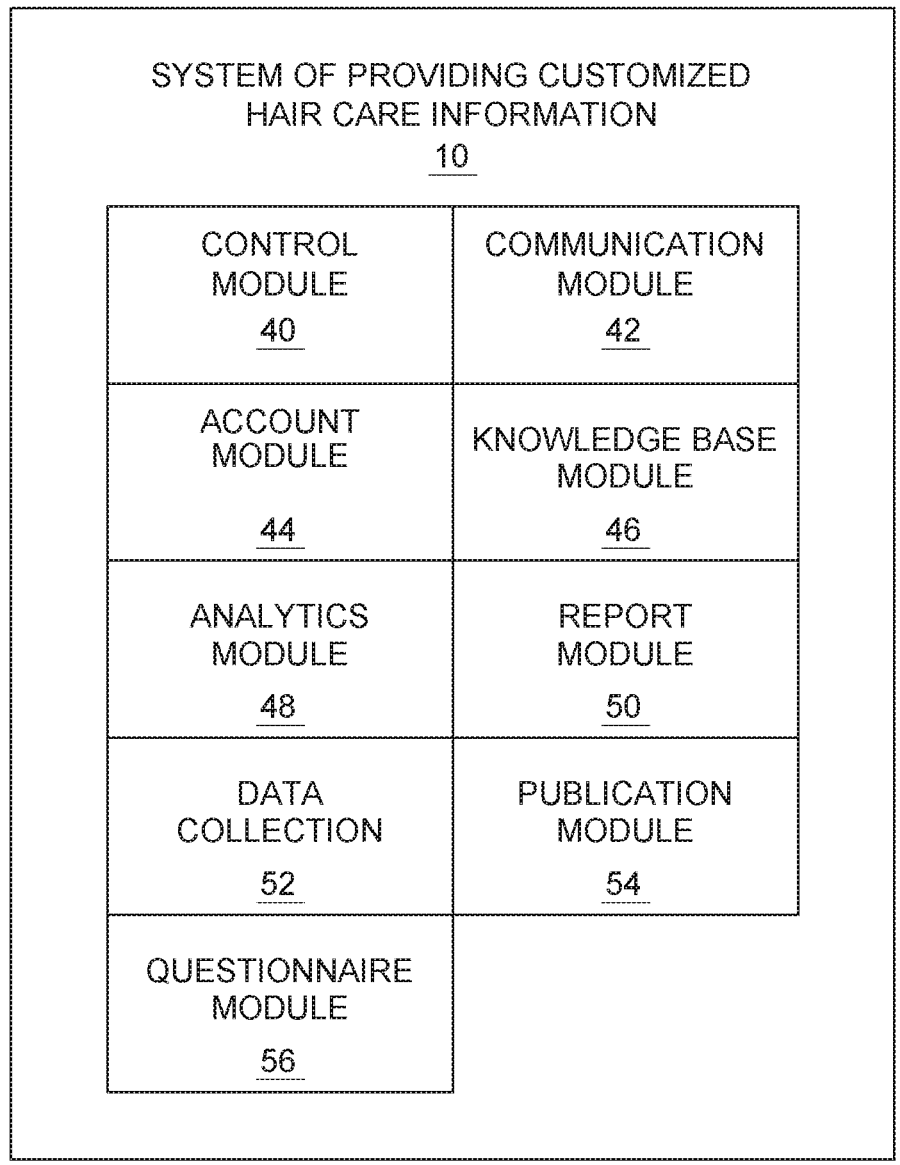
FIG. 3 is a module diagram of a system of providing customized hair care information, according to one embodiment of the invention.

FIG. 3 is a module diagram of a system for providing customized hair care information, according to one embodiment of the invention. There is shown a system for providing customized hair care information 10 including a control module 40, a communication module 42, an account module 44, a knowledge base module 46, an analytics module 48, a report module 50, a data collection module 52, a publication module 54, and a questionnaire module 56.

The illustrated system of providing customized hair care information 10 includes an account module 44 that stores hair data in association with a plurality of accounts. The account module 44 is configured to manage a plurality of user accounts of the system. The account module 44 is configured to store and update user hair profile data. Non-limiting examples of an account module may be an account creation module as described in U.S. Patent Publication No.: 2008/0281617, by Conrad et al.; or an account management system as described in U.S. Patent Publication No.: 2003/0028790, by Bleumer et all which are incorporated for their supporting teachings herein.

The system 10 includes a control module 40 functionally coupled to the modules and components of the system 10 as required to function. The control module is configured to manage operational controls, standards, parameters, or settings of the system 10. Non-limiting examples of a control module may be a control module described in U.S. Pat. No. 5,430,836, issued to Wolf et al.; or a control module described in U.S. Pat. No. 6,243,635, issued to Swan et al. which are incorporated for their supporting teachings herein. A control module may include but is not limited to a processor, a state machine, a script, a decision tree, and the like.

The system 10 includes a communication module 42 in communication with one or more other modules and components of the system 10 and/or in communication with one or more outside modules such as but not limited to a communication module of another user over a computerized network, such as but not limited to a smartphone. Such communication may be wireless, especially in regards to communications over a network, and/or may be wired and/or over a bus, such as may generally be found within a portable communication device. The communication module may include instructions for communication protocol(s) such as but not limited to TCP/IP, Bluetooth, distributed communication networks, and the like and combinations thereof. The communication module may also be configured to provide a secure method of communication over a computerized network. Non-limiting examples of a communication module may be but not limited to: a communication module described in U.S. Pat. No. 5,307,463, issued to Hyatt et al.; or a communication module described in U.S. Pat. No. 6,133,886, issued to Fariello et al. which are incorporated for their supporting herein.

The system 10 includes a knowledge base module 46 that includes executable information regarding hair. The system 10 includes an analytics module 48 in communication with each of the account module 44 and the knowledge base module 46 and analyzes collections of hair data according to the executable information regarding hair. The analytics module 48 analyzes stored data from a plurality of diverse accounts thereby generating group account analytics. An analysis module in communication with the modules and components of the adaptive engine module. The analytics module is configured to analyze user hair data from a questionnaire module or other type of hair gathering technique to determine which type of hair best matches the user, based on the user's answers from the questions from the questionnaire module. Non-limiting examples of analytics module may be a data analysis system as described in U.S. Patent Publication No.: 2012/0290576; or an analysis system as described in U.S. Patent Publication No.: 2011/0208519, which are incorporated for their supporting teachings herein. Non-limiting examples of a knowledge base module may be as described in U.S. Pat. No. 6,064,971 by Hartnett and U.S. Pat. No. 5,257,185 by Farley, which are incorporated for their supporting teachings herein.

The system 10 includes a report module 50 in communication with the analytics module 48 that automatically generates a report including analysis information from the analytics module 48. The report module 50 is in communication with the account module 44. The report module 50 automatically sends the report to an electronic address listed within the account module 44 that is associated with the hair data analyzed in the report. The report module 50 groups the analyzed stored data by at least one category selected from the group of categories consisting of: race/ethnicity, hair color, hair composition, hair style, hair length, hair thickness, and hair curliness. The report module is in communication with the modules and components of the system 10. The report module is configured to sort and format hair data from the analytics module by the user to view in a report. The report module is configured to set parameters, criteria, characteristics, settings, preferences, listings, categories, groupings, etc. for the report. Non-limiting examples of a report module may be a system as described in U.S. Pat. No. 7,711,581; or a report generation module as described in U.S. Patent Publication No.: 2012/0284188, which are incorporated for their supporting teachings herein.

The system 10 includes a data collection device 52 that is in communication with the account module 44 and automatically collects data on hair samples and delivers such data to the account module 44. The data collection module is in communication with the plurality of user interface modules and the modules and components of the system. The data collection module is configured to collect and store data for each of the plurality of user interfaces and each profile or account associated therewith, in addition to a hair profile. The data collection module is in communication with the various modules and components of the system and configured to store data transferred there through. The data collection module is configured to store data transferred through each of the user interface modules, thereby updating the system with up to data and real time hair data. The data collection module is configured to securely store hair profile and account data along with data transferred therethrough. Data collection modules may be databases or data files and the memory storage device may be hard drives or tapes. A non-limiting example of a data base is Filemaker Pro 11, manufactured by Filemaker Inc., 5261 Patrick Henry Dr., Santa Clara, Calif., 95054. Non-limiting examples of a data collection module may include: a HP Storage Works P2000 G3 Modular Smart Array System, manufactured by Hewlett-Packard Company, 3000 Hanover Street, Palo Alto, Calif., 94304, USA; or a Sony Pocket Bit USB Flash Drive, manufactured by Sony Corporation of America, 550 Madison Avenue, New York, N.Y., 10022.

The system 10 includes a publication module 54 that is in communication with the report module 50 that publishes report information to a plurality of electronic addresses. Non-limiting examples of a publishing module may be a system as described in U.S. Patent Publication No.: 2012/0310884; or a publishing module as described in U.S. Patent Publication No.: 2008/0228507, which are incorporated for their supporting teachings herein.

The system 10 includes a questionnaire module 56 that includes an electronic questionnaire functionally coupled to the account module 44.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. A method of providing customized hair care information, comprising the steps of:
   a) gathering data on an individual's hair, including each of:
      i. at least one dimensional characteristic selected from: average diameter, average cross-sectional area, and ellipticity;
      ii. at least one kinetic characteristic selected from: tensile strength, plateau load, plateau stress, post-yield modulus, load at strain stress at strain, work at strain, break load, break stress, break extension, and twisting frequency;
      iii. hair porosity; and
      iv. and at least one individual characteristic selected from: demographic, hair care condition, hair care practice, location, hair care history, and health history;
   b) creating, within a computerized system, an account;
   c) storing the gathered data in association with the account in a computerized data storage device;
   d) analyzing the stored data using a processor in association with a computerized knowledge base thereby generating account analytics by searching the computerized knowledge base for similar prior hair samples not associated with the account that observed positive changes after specific treatments;
   e) automatically generating a customized hair report based on the account analytics including one or more specific treatments associated with similar prior hair samples; and
   f) automatically feeding the computerized knowledge base with anonymized additional information associated with the gathered data including treatment information.

2. The method of claim 1, further comprising the step of analyzing stored data from a plurality of diverse accounts thereby generating group account analytics.

3. The method of claim 1, further comprising the step of automatically publishing information associated with account analytics over a computerized network.

4. The method of claim 1, wherein the step of gathering data includes each of the steps of:
   a) gathering a hair sample;
   b) conducting an interview with an individual; and
   c) completing a questionnaire based upon an individual's hair.

5. The method of claim 1, wherein the step of storing the gathered data includes the step of automatically storing the gathered data with an account, over a computerized network.

6. The method of claim 2, wherein the step of analyzing stored data from a plurality of diverse accounts includes the step of grouping the analyzed stored data by at least one category selected from the group of categories consisting of: race/ethnicity, hair color, hair composition, hair style, hair length, hair thickness, and hair curliness.

7. A system of providing customized hair care information, comprising:
   a) an account module, including a data storage device, that stores anonymized hair data therein in association with a plurality of accounts, the anonymized hair data including at least dimensional, kinetic, and porosity of hair;
   b) a knowledge base module including executable information regarding hair including hair samples that observed positive changes after specific treatments;
   c) an analytics module, including a processor, in communication with each of the account module and the knowledge base module and that analyzes collections of hair data according to the executable information regarding hair and searches the knowledge base module for similar hair samples and returns specific treatments associated with the similar hair samples;
   d) a report module in communication with the analytics module that automatically generates a report including analysis information from the analytics module including specific treatments associated with similar prior hair samples; and
   e) a plurality of hair data measurement devices functionally coupled to the analytics module such that data obtained thereby may be utilized thereby, including a device that measures a dimensional characteristic of hair, a device that measures a kinetic characteristic of hair, and a device that measures porosity of hair.

8. The system of claim 7, wherein the hair data measurement devices includes at least one of: a micrometer, a stereo microscope, a density meter, and a gas sorption instrument.

9. The system of claim 8, wherein the report module automatically sends the report to an electronic address listed within the account module that is associated with the hair data analyzed in the report.

10. The system of claim 7, further comprising a data collection device in communication with the account module and that automatically collects data on hair samples and delivers such data to the account module.

11. The system of claim 7, further comprising a publication module in communication with the report module that publishes report information to a plurality of electronic addresses.

12. The system of claim 7, wherein the report module groups the analyzed stored data by at least one category selected from the group of categories consisting of: race/ethnicity, hair color, hair composition, hair style, hair length, hair thickness, and hair curliness.

13. The system of claim 7, wherein the analytics module analyzes stored data from a plurality of diverse accounts thereby generating group account analytics.

14. The system of claim 7, further comprising a questionnaire module including an electronic questionnaire functionally coupled to the account module.

15. A system of providing customized hair care information, comprising:
   a) an account module that stores anonymized hair data and grooming data in association with a plurality of accounts within a data storage device;
   b) a knowledge base module including executable information regarding hair;
   c) an analytics module in communication with each of the account module and the knowledge base module and that analyzes collections of hair data, using a processor, according to the executable information regarding hair and automatically feeds the knowledge base module with additional information associated with the gathered data including treatment information;
   d) a report module in communication with the analytics module and the accounts module that automatically generates a report including analysis information from the analytics module; and
   e) a data collection hardware system in communication with the account module and that automatically collects durability data on hair samples and delivers such data to the account module, wherein the durability data includes porosity data together with kinetic data and dimensional data.

16. The system of claim 15, wherein the report module automatically sends the report to an electronic address listed within the account module that is associated with the hair data analyzed in the report and wherein durability data on hair samples includes at least three of the data consisting of: tensile strength, plateau load, plateau stress, post-yield modulus, load at strain stress at strain, work at strain, break load, break stress, break extension, average diameter, average cross-sectional area, ellipticity, and twisting frequency.

17. The system of claim 16, further comprising a data collection device in communication with the account module and that automatically collects data on hair samples and delivers such data to the account module.

18. The system of claim 17, wherein the report module groups the analyzed stored data by at least one category selected from the group of categories consisting of: race/ethnicity, hair color, hair composition, hair style, hair length, hair thickness, and hair curliness.

19. The system of claim 18, wherein the analytics module analyzes stored data from a plurality of diverse accounts thereby generating group account analytics.

20. The system of claim 19, further comprising a questionnaire module including an electronic questionnaire functionally coupled to the account module.

* * * * *